(12) United States Patent
Aoki et al.

(10) Patent No.: US 8,551,509 B2
(45) Date of Patent: Oct. 8, 2013

(54) SKIN AGENT FOR EXTERNAL USE AND COSMETIC AGENT INCLUDING UBIQUINONE DERIVATIVE OR SALT THEREOF AND METHOD USING THE SAME

(75) Inventors: Hirobumi Aoki, Chiba (JP); Yohei Kurata, Kawasaki (JP); Harumi Kamachi, Chiba (JP); Hirotsugu Nakanishi, Chiba (JP)

(73) Assignee: Showa Denko K.K., Tokyo (JP)

( * ) Notice: Subject to any disclaimer, the term of this patent is extended or adjusted under 35 U.S.C. 154(b) by 635 days.

(21) Appl. No.: 12/445,184

(22) PCT Filed: Oct. 12, 2007

(86) PCT No.: PCT/JP2007/070385
§ 371 (c)(1),
(2), (4) Date: Apr. 10, 2009

(87) PCT Pub. No.: WO2008/047882
PCT Pub. Date: Apr. 24, 2008

(65) Prior Publication Data
US 2010/0074879 A1    Mar. 25, 2010

(30) Foreign Application Priority Data

Oct. 13, 2006  (JP) .................................. 2006-280112
Oct. 10, 2007  (JP) .................................. 2007-264317

(51) Int. Cl.
*A61K 8/02* (2006.01)
*A61K 38/43* (2006.01)
*C07C 39/10* (2006.01)
*C07F 9/02* (2006.01)

(52) U.S. Cl.
USPC ............. 424/401; 424/94.1; 568/763; 568/17

(58) Field of Classification Search
None
See application file for complete search history.

(56) References Cited

U.S. PATENT DOCUMENTS

| | | | | |
|---|---|---|---|---|
| 2,962,519 A | * | 11/1960 | Folkers et al. | 558/162 |
| 3,127,434 A | * | 3/1964 | Andrews | 558/198 |
| 2004/0052754 A1 | * | 3/2004 | West et al. | 424/70.23 |

FOREIGN PATENT DOCUMENTS

| JP | 58180410 A | 10/1983 |
|---|---|---|
| JP | 2006016305 A | 1/2006 |
| JP | 2006089422 A | 4/2006 |
| WO | 88/03015 A1 | 5/1988 |
| WO | 9617626 A2 | 6/1996 |
| WO | 03061395 A1 | 7/2003 |

* cited by examiner

*Primary Examiner* — Chris R Tate
*Assistant Examiner* — Russell Fiebig
(74) *Attorney, Agent, or Firm* — Sughrue Mion, PLLC

(57) ABSTRACT

A skin agent for external use and a cosmetic agent are provided, by transdermal administration of which expected actions and effects of ubiquinone derivatives, salts thereof, ubiquinones and ubiquinols are effectively obtained.

The skin agent for external use includes a ubiquinone derivative or a salt thereof as an active ingredient. The ubiquinone derivative is represented by the formula (1):

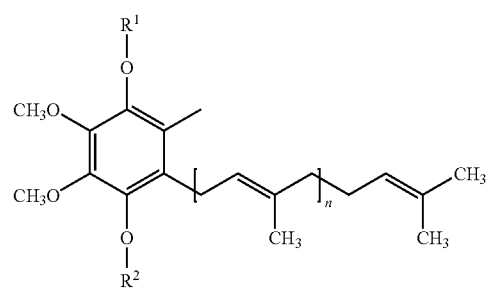

(1)

wherein $R^1$ and $R^2$ are each a hydrogen atom or a phosphoric group, at least one of $R^1$ and $R^2$ is a phosphoric group, and n is an integer in the range of 1 to 9.

17 Claims, No Drawings

SKIN AGENT FOR EXTERNAL USE AND COSMETIC AGENT INCLUDING UBIQUINONE DERIVATIVE OR SALT THEREOF AND METHOD USING THE SAME

TECHNICAL FIELD

The present invention relates to a skin agent for external use and a cosmetic agent including a ubiquinone derivative modified with a phosphoric group or a salt of the derivative. The present invention also relates to a method for supplying skin cells with the ubiquinone derivative or salt thereof, ubiquinone itself or ubiquinol.

BACKGROUND ART

Ubiquinone is a naturally-derived component that is also commonly known as coenzyme Q. Coenzyme Q10 is 2,3-dimethoxy-5-methyl-6-polyprenyl-1,4-benzoquinone in which the number of side-chain isoprene units is 10, and is a ubiquinone peculiar to human beings. This compound is named ubidecarenone in the Japanese pharmacopoeia, coenzyme Q10 as a food additive, and ubiquinone as a cosmetic material.

Ubiquinone is an essential coenzyme for energy production in mitochondria and is an important substance in a living organism as an anti oxidizing substance. It is confirmed that ubiquinone is effective for heart disease, hypertension and rheumatic valve disease, probably because ubiquinone improves cell metabolism. In addition, ubiquinone improves skin roughness and is used in cosmetic agents as described in Patent Document 1.

Ubiquinone has very low water solubility and has high crystallinity. Consequently, formulating ubiquinone is difficult in general. Ubiquinone dissolves well in nonpolar hydrocarbons such as ether and hexane, but shows very low solubility in other solvents. A large number of methods have been proposed for dispersing ubiquinone in a system by using various assistants such as surfactants and clathrating agents. However, these methods have many restrictions on prescription. Further, the obtainable products have low physical stability and long-term storage results in separation or precipitation. Increasing the ubiquinone concentration will be effective for ensuring or improving effects of ubiquinone preparations. However, because of the poor water solubility and high crystallinity, it has been difficult to ensure a sufficient concentration of ubiquinone in an aqueous agent that is the most frequent formulation.

Ubiquinol occurs when ubiquinone is reduced with two hydrogen atoms. This compound is said to be more effective for antioxidation than ubiquinone. Application of ubiquinol in food has been studied. Patent Document 2 discloses ubiquinol-rich fatty food, and Patent Document 3 describes health food containing ubiquinol. Patent Document 4 discloses a dermatological preparation containing ubiquinol.

The water solubility of ubiquinol only slightly surpasses that of ubiquinone. Because of high antioxidant ability, ubiquinol is more unstable to oxidation and is easily oxidized in the air into ubiquinone. The poor water solubility and easy oxidation make formulating ubiquinol more difficult than formulating ubiquinone.

To improve the poor water solubility of ubiquinone, the hydrophilicity of ubiquinone is increased by chemical modification by introducing polar groups. Patent Document 5 discloses a water-soluble ubiquinone prodrug in which ubiquinone is substituted with hydrophilic groups. However, the formulations of hydrophilic ubiquinone have been limited to oral administration and injection administration, and the knowledge of hydrophilic ubiquinone has been very little. There has been no knowledge of transdermal administration of hydrophilic ubiquinone, and the use of ubiquinone as a skin agent for external use has never been anticipated.

The hydrophilic ubiquinone prodrug is expected to produce effects when the polar group-modified ubiquinone is converted by the enzyme activity in the body into antioxidant ubiquinone and ubiquinol.

It has never been anticipated that the hydrophilic ubiquinone derivative itself possesses higher radical scavenging ability than ubiquinone, and prevents skin oxidation, namely skin aging.

Patent Document 1: Japanese Patent Application Laid-Open Publication No. S58-180410

Patent Document 2: WO 2003/061395

Patent Document 3: Japanese Patent Application Laid-Open Publication No. 2006-89422

Patent Document 4: Japanese Patent Application Laid-Open Publication No. 2006-16305

Patent Document 5: WO 96/17626

DISCLOSURE OF THE INVENTION

Problems to be Solved by the Invention

An object of the present invention is to provide a skin agent for external use and a cosmetic agent which include a ubiquinone derivative or a salt thereof and through transdermal administration of which the ubiquinone derivative or the salt thereof, or ubiquinone or ubiquinol effectively produces expected actions and effects. Another object of the present invention is to provide a method for supplying skin cells with a ubiquinone derivative or a salt thereof, or ubiquinone or ubiquinol by applying the skin agent for external use or the cosmetic agent.

Means for Solving the Problems

The present inventors have studied diligently in order to achieve the above objects. It has been found that a ubiquinone derivative modified with a phosphoric group or a salt thereof has high solubility in water and can be favorably formulated into an aqueous skin agent for external use or an aqueous cosmetic agent in high concentration. It has been also found that the ubiquinone derivative or the salt thereof is effectively incorporated into skin cells, and that the derivative itself has high antioxidant ability and is rapidly converted to ubiquinone and to ubiquinol that is largely responsible for the antioxidant ability of the skin agent or the cosmetic agent. More specifically, the present invention is directed to the following.

[1] A skin agent for external use comprising at least one component selected from the group consisting of ubiquinone derivatives and salts thereof, the ubiquinone derivatives being represented by the formula (1):

[Chem. 1]

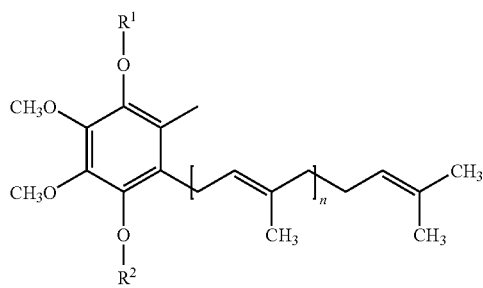

(1)

wherein $R^1$ and $R^2$ are each a hydrogen atom or a phosphoric group, at least one of $R^1$ and $R^2$ is a phosphoric group, and n is an integer in the range of 1 to 9.

[2] The skin agent for external use as defined in above [1], wherein the at least one component selected from the group consisting of the ubiquinone derivatives and the salts thereof is contained in a concentration in the range of 0.0005 to 50% by mass.

[3] The skin agent for external use as defined in above [1], wherein in the formula (1), $R^1$ and $R^2$ are both phosphoric groups and n is 9.

[4] A cosmetic agent comprising at least one component selected from the group consisting of ubiquinone derivatives and salts thereof, the ubiquinone derivatives being represented by the formula (1):

[Chem. 2]

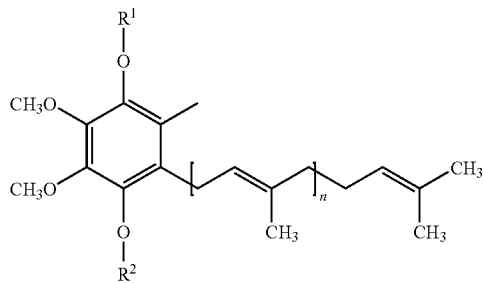

(1)

wherein $R^1$ and $R^2$ are each a hydrogen atom or a phosphoric group, at least one of $R^1$ and $R^2$ is a phosphoric group, and n is an integer in the range of 1 to 9.

[5] The cosmetic agent as defined in above [4], wherein the at least one component selected from the group consisting of the ubiquinone derivatives and the salts thereof is contained in a concentration in the range of 0.0005 to 50% by mass.

[6] The cosmetic agent as defined in above [4], wherein the cosmetic agent is an antioxidant cosmetic agent.

[7] The cosmetic agent as defined in above [4], wherein the cosmetic agent is an anti aging cosmetic agent.

[8] The cosmetic agent as defined in above [4], wherein the cosmetic agent is a skin roughness preventing cosmetic agent.

[9] A method for supplying skin cells with at least one selected from the group consisting of ubiquinone derivatives, salts of the ubiquinone derivatives, ubiquinone and ubiquinol, the method comprising applying to skin at least one component selected from the group consisting of ubiquinone derivatives and salts thereof, the ubiquinone derivatives being represented by the formula (1):

[Chem. 3]

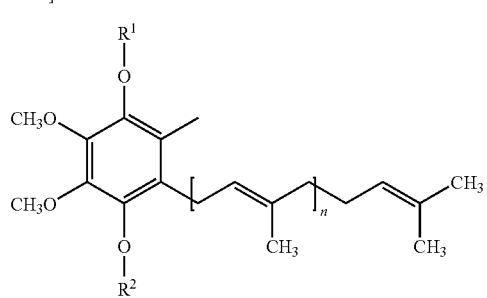

(1)

wherein $R^1$ and $R^2$ are each a hydrogen atom or a phosphoric group, at least one of $R^1$ and $R^2$ is a phosphoric group, and n is an integer in the range of 1 to 9.

[10] The method as defined in above [9], wherein at least one of ubiquinone and ubiquinol is formed by dephosphorylation of the ubiquinone derivative or the salt thereof applied to the skin.

[11] The method as defined in above [9], wherein ubiquinone is formed by oxidation of ubiquinol.

[12] The method as defined in above [9], wherein the at least one component selected from the group consisting of the ubiquinone derivatives and the salts thereof is applied to the skin by using the skin agent for external use as defined in above [1].

[13] The method as defined in above [9], wherein the at least one component selected from the group consisting of the ubiquinone derivatives and the salts thereof is applied to the skin by using the cosmetic agent as defined in above [4].

[14] A method for accelerating the regeneration of stratum corneum, which uses at least one component selected from the group consisting of ubiquinone derivatives and salts thereof, the ubiquinone derivatives being represented by the formula (1):

[Chem. 4]

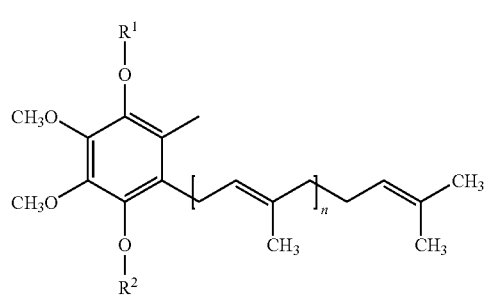

(1)

wherein $R^1$ and $R^2$ are each a hydrogen atom or a phosphoric group, at least one of $R^1$ and $R^2$ is a phosphoric group, and n is an integer in the range of 1 to 9.

[15] A method for improving skin roughness, which uses at least one component selected from the group consisting of ubiquinone derivatives and salts thereof, the ubiquinone derivatives being represented by the formula (1):

[Chem. 5]

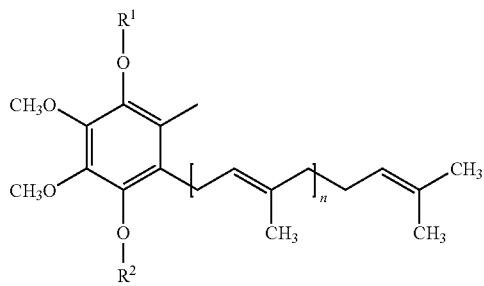

(1)

wherein R¹ and R² are each a hydrogen atom or a phosphoric group, at least one of R¹ and R² is a phosphoric group, and n is an integer in the range of 1 to 9.

[16] A method for preventing skin aging, which uses at least one component selected from the group consisting of ubiquinone derivatives and salts thereof, the ubiquinone derivatives being represented by the formula (1):

[Chem. 6]

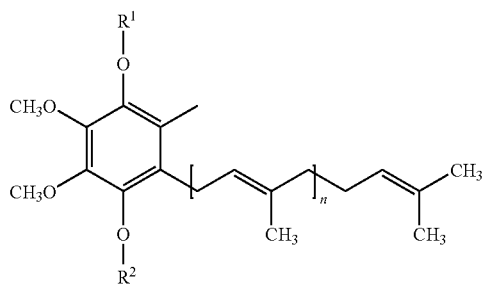

(1)

wherein R¹ and R² are each a hydrogen atom or a phosphoric group, at least one of R¹ and R² is a phosphoric group, and n is an integer in the range of 1 to 9.

[17] A method for scavenging radicals, which uses at least one component selected from the group consisting of ubiquinone derivatives and salts thereof, the ubiquinone derivatives being represented by the formula (1):

[Chem. 7]

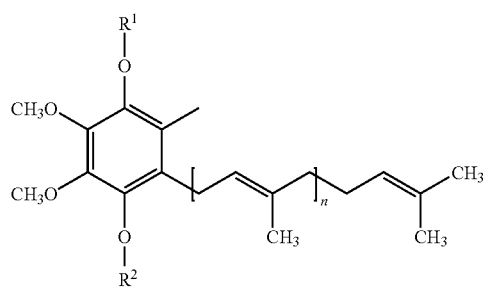

(1)

wherein R¹ and R² are each a hydrogen atom or a phosphoric group, at least one of R¹ and R² is a phosphoric group, and n is an integer in the range of 1 to 9.

Advantages of the Invention

The ubiquinone derivatives modified with a phosphoric group and the salts thereof according to the present invention have high water solubility and can be formulated into an aqueous skin agent for external use or an aqueous cosmetic agent in high concentration. By transdermal administration of the aqueous skin agent or cosmetic agent, the ubiquinone derivative or the salt thereof is incorporated into skin cells as such to prevent oxidation. In the skin cells, the ubiquinone derivative or the salt thereof is converted into ubiquinone and into ubiquinol which is responsible for the antioxidant ability of the skin agent or the cosmetic agent.

BEST MODE FOR CARRYING OUT THE INVENTION

The following describes the skin agent for external use, the cosmetic agent, and the method for supplying skin cells with a ubiquinone derivative or a salt thereof, or ubiquinone or ubiquinol by applying the skin agent for external use or the cosmetic agent.

The skin agent for external use or the cosmetic agent according to the present invention includes a ubiquinone derivative or a salt thereof. The ubiquinone derivative is represented by the formula (1):

[Chem. 8]

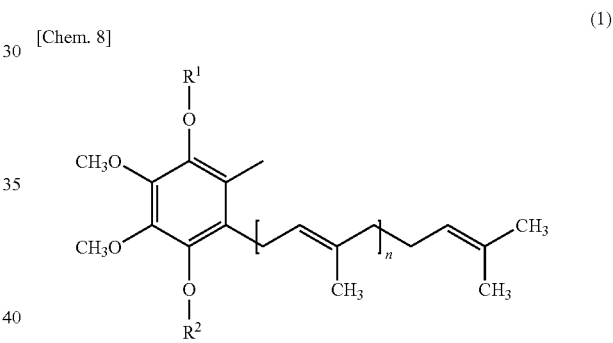

(1)

wherein R¹ and R² are each a hydrogen atom or a phosphoric group, at least one of R¹ and R² is a phosphoric group, and n is an integer in the range of 1 to 9.

Such ubiquinone derivative modified with a phosphoric group (hereafter, simply referred to as the ubiquinone derivative) may be obtained by an established method. For example, the quinone group of ubiquinone is reduced into a quinol group, and the hydroxyl group is phosphorylated by a usual method. Such synthesis is disclosed in U.S. Pat. No. 2,962,519.

The ubiquinone derivatives are much more soluble in water than ubiquinones. For example, while the ubiquinone in which the number of side-chain isoprene units is 10 has water solubility of less than 100 ppm at normal temperature, a derivative thereof modified with two phosphoric groups shows water solubility of more than 1%. That is, the water solubility of phosphorylated ubiquinone derivatives is much more than 100 times that of the ubiquinones. They can therefore be easily formulated into stable aqueous preparations in a high concentration without precipitation. Furthermore, the aqueous preparations of the phosphorylated ubiquinone derivatives have radical scavenging ability higher than achieved with the ubiquinones. The skin agents for external use containing such derivatives possess high antioxidant ability.

The ubiquinone derivatives may be in the form of salt. Examples of cations capable of forming a salt in combination with an anion of the phosphoric group of the ubiquinone derivative include sodium ion, potassium ion, calcium ion, magnesium ion, zinc ion and ammonium ion. Among them, sodium ion and potassium ion are more suited for use in skin agents for external use, in particular cosmetic agents.

The ubiquinone derivatives are used singly or in combination with the salts of the ubiquinone derivatives.

When the ubiquinone derivative is incorporated into human skin cells, it is converted into corresponding ubiquinone and ubiquinol. More specifically, it is thought that the ubiquinone derivative administered into the cells is rapidly dephosphorylated in the cells to give ubiquinone via primary product ubiquinol. The free ubiquinol in the cells is oxidized into ubiquinone. This ubiquinone, like ubiquinones administered by conventional methods, will be reduced into ubiquinol in the cells, and this cycle will improve the capacity of oxidation and reduction. By such mechanism, the present invention provides advantages comparable to those obtained by administration of ubiquinone formulations prepared by the conventional methods.

In addition to the ubiquinone derivative or the salt thereof, the skin agent for external use and the cosmetic agent according to the present invention may contain as required components that are generally used in skin agents for external use and cosmetic agents while still achieving the advantages of the present invention.

Such components include the following:

hydrocarbons such as ozokerite, α-olefin oligomers, light isoparaffin, light liquid isoparaffin, squalene, squalane, synthetic squalane, vegetable squalane, ceresin, paraffin, polyethylene, polybutene, microcrystalline wax, liquid isoparaffin, liquid paraffin, mineral oil and vaseline;

natural waxes such as jojoba oil, carnauba wax, candelilla wax, rice bran wax, shellac, lanolin, mink oil wax, whale wax, sugarcane wax, sperm oil, beeswax and montan wax;

natural fats and oils such as avocado oil, almond oil, olive oil, extra virgin olive oil, sesame oil, rice bran oil, rice oil, rice germ oil, corn oil, soybean oil, maize oil, persic oil, palm kernel oil, palm oil, castor oil, grape seed oil, cotton seed oil, coconut oil, hydrogenated coconut oil, beef tallow, hydrogenated oil, horse oil, mink oil, egg yolk oil, egg yolk fatty oil, rose hip oil, kukui nut oil, evening primrose oil, wheat germ oil, peanut oil, camellia oil, sasanqua oil, cacao butter, Japanese wax, beef bone fat, neatsfoot oil, lard, horse fat, mutton tallow, Shea butter, macadamia nut oil and meadowfoam oil;

fatty acids such as lauric acid, myristic acid, palmitic acid, stearic acid, behenic acid, oleic acid, isostearic acid, 12-hydroxystearic acid, undecylenic acid and coconut fatty acid;

higher alcohols such as isostearyl alcohol, octyldodecanol, hexyldecanol, cholesterol, phytosterol, lauryl alcohol, myristyl alcohol, cetanol, stearyl alcohol, oleyl alcohol, behenyl alcohol and cetostearyl alcohol;

alkyl glyceryl ethers such as batyl alcohol, chimyl alcohol, selachyl alcohol and isostearyl glyceryl ether;

esters such as isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyloleate, oleyloleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol di(caprylate caprate), propylene glycol dicaprate, propylene glycol dioleate, neopentyl glycol dicaprate, neopentyl glycol dioctanoate, glyceryl tricaprylate, glyceryl tri-2-ethylhexanoate, glyceryl tri(caprylate caprate), glyceryl tri(caprylate caprate stearate), glyceryl triundecylate, glyceryl triisopalmitate, glyceryl triisostearate, trimethylolpropane tri-2-ethylhexanoate, trimethylolpropane triisostearate, pentaerythrityl tetra-2-ethylhexanoate, pentaerythrityl tetramyristate, pentaerythrityl tetraisostearate, diglyceryl tetraisostearate, octyldodecyl neopentanoate, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, cetyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di-2-ethylhexyl succinate, diisopropyl adipate, diisobutyl adipate, dioctyl adipate, diheptylundecyl adipate, diethyl sebacate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate, isostearyl 12-stearoylhydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate and isotridecyl isononanoate;

silicone oils such as methyl polysiloxane, methylphenyl polysiloxane, methylhydrogen polysiloxane, methyl cyclopolysiloxane, octamethyl cyclotetrasiloxane, decamethyl cyclopentasiloxane, dodecamethyl cyclohexasiloxane, octamethyl trisiloxane, decamethyl tetrasiloxane, tetradecamethyl hexasiloxane, highly polymerized methyl polysiloxane, dimethyl siloxane/methyl(polyoxyethylene)siloxane/methyl(polyoxypropylene)siloxane copolymer, dimethyl siloxane/methyl(polyoxyethylene)siloxane copolymer, dimethyl siloxane/methyl(polyoxypropylene)siloxane copolymer, dimethyl siloxane/methyl cetyloxysiloxane copolymer, dimethyl siloxane/methyl stearoxysiloxane copolymer, polyether-modified silicones, alcohol-modified silicones, alkyl-modified silicones and amino-modified silicones;

polymers such as sodium alginate, carrageenan, agar, furcelleran, cyamoposis gum, pyrus cyclonia seed, konjac mannan, tamarind gum, tara gum, dextrin, starch, locust bean gum, gum arabic, ghatti gum, karaya gum, tragacanth gum, arabinogalactan, pectin, marmelo, chitosan, starch, curdlan, xanthan gum, gellan gum, cyclodextrin, dextran, pullulan, microcrystalline cellulose, methylcellulose, ethylcellulose, hydroxyethylcellulose, hydroxypropylcellulose, hydroxypropylmethylcellulose, carboxymethylcellulose, carboxy starch, cationized cellulose, starch phosphate, cationized cyamoposis gum, carboxymethyl/hydroxypropylated cyamoposis gum, hydroxypropylated cyamoposis gum, albumin, casein, gelatin, sodium polyacrylate, polyacrylic acid amide, carboxyvinyl polymers, polyethyleneimine, highly polymerized polyethylene glycol, polyvinyl alcohol, polyvinylpyrrolidone, polyvinyl ether, polyacrylamide, acrylic acid copolymers, methacrylic acid copolymers, maleic acid copolymers, vinylpyridine copolymers, ethylene/acrylic acid copolymers, vinylpyrrolidone polymers, vinyl alcohol/vinylpyrrolidone copolymers, nitrogen-substituted acrylamide polymers, amino-modified silicones, cationized polymers, dimethylacryl ammonium polymers, acrylic acid-based anionic polymers, methacrylic acid-based anionic polymers, modified silicones, alkyl($C_{10-30}$)acrylate or methacrylate copolymers and polyoxyethylene/polyoxypropylene copolymer;

lower alcohols such as ethanol, isopropyl alcohol, 1-butanol, 2-butanol and benzyl alcohol;

polyhydric alcohols such as ethylene glycol, diethylene glycol, polyethylene glycol, propylene glycol, polypropylene glycol, glycerol, diglycerol, polyglycerol, 1,3-butanediol, triethylene glycol, dipropylene glycol, 3-methyl-1,3-butanediol, 1,2-pentanediol, 1,4-pentanediol, 1,5-pentanediol, 2,4-pentanediol, 2-methyl-2,4-pentanediol, 3-methyl-1,5-pentanediol, 1,2-hexanediol and 1,6-hexanediol;

anionic surfactants such as potassium coconut fatty acid ester, sodium coconut fatty acid ester, triethanolamine coconut fatty acid ester, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, sodium castor oil fatty acid ester, zinc undecylenate, zinc laurate, zinc myristate, magnesium myristate, zinc palmitate, zinc stearate, calcium stearate, magnesium stearate, aluminum stearate, calcium myristate, magnesium myristate, aluminum dimyristate, aluminum isostearate, polyoxyethylene laurylether acetic acid, sodium polyoxyethylene laurylether acetate, polyoxyethylene tridecylether acetic acid, sodium polyoxyethylene tridecylether acetate, sodium stearoyl lactate, sodium isostearoyl lactate, lauroylsarcosine sodium, sarcosine coconut fatty acid ester, sarcosine sodium coconut fatty acid ester, sarcosine triethanolamine coconut fatty acid ester, lauroyl sarcosine, lauroyl sarcosine potassium, lauroyl sarcosine triethanolamine, oleoyl sarcosine, myristoyl sarcosine sodium, sodium stearoyl glutamate, coconut fatty acid acylglutamic acid, coconut fatty acid potassium acylglutamate, coconut fatty acid sodium acylglutamate, coconut fatty acid triethanolamine acylglutamate, lauroyl acylglutamic acid, potassium lauroyl acylglutamate, sodium lauroyl acylglutamate, triethanolamine lauroyl acylglutamate, myristoyl acylglutamic acid, potassium myristoyl acylglutamate, sodium myristoyl acylglutamate, stearoyl acylglutamic acid, potassium stearoyl acylglutamate, disodium stearoyl acylglutamate, hydrogenated tallow fatty acid sodium acylglutamate, coconut fatty acid/hydrogenated tallow fatty acid sodium acylglutamate, methylalanine sodium coconut fatty acid ester, lauroyl methylalanine, lauroyl methylalanine sodium, lauroyl methylalanine triethanolamine, myristoyl methylalanine sodium, lauroyl methyltaurine sodium, methyltaurine potassium coconut fatty acid ester, methyltaurine sodium coconut fatty acid ester, methyltaurine magnesium coconut fatty acid ester, myristoyl methyltaurine sodium, palmitoyl methyltaurine sodium, stearoyl methyltaurine sodium, oleoyl methyltaurine sodium, sodium alkanesulfonate, sodium tetradecenesulfonate, dioctylsodium sulfosuccinate, lauryl disodium sulfosuccinate, ethyl coconut fatty acid ester sodium sulfonate, sodium laurylsulfate, triethanolamine laurylsulfate, sodium cetyl sulfate, triethanolamine alkyl (11, 13, 15) sulfates, sodium alkyl (12, 13) sulfates, triethanolamine alkyl (12, 13) sulfates, ammonium alkyl (12, 14, 16) sulfates, diethanolamine alkyl (12, 13) sulfates, triethanolamine alkyl (12-14) sulfates, triethanolamine alkyl (12-15) sulfates, magnesium triethanolamine cocoalkylsulfate, ammonium laurylsulfate, potassium laurylsulfate, magnesium laurylsulfate, monoethanolamine laurylsulfate, diethanolamine laurylsulfate, sodium myristylsulfate, sodium stearylsulfate, sodium oleylsulfate, triethanolamine oleylsulfate, sodium polyoxyethylene laurylether sulfate, triethanolamine polyoxyethylene laurylether sulfate, sodium polyoxyethylene (1) alkyl (11, 13, 15) ether sulfate, triethanolamine polyoxyethylene (1) alkyl (11, 13, 15) ether sulfate, sodium polyoxyethylene (3) alkyl (11-15) ether sulfate, sodium polyoxyethylene (2) alkyl (12, 13) ether sulfate, sodium polyoxyethylene (3) alkyl (12-14) ether sulfate, sodium polyoxyethylene (3) alkyl (12-15) ether sulfate, sodium polyoxyethylene (2) laurylether sulfate, sodium polyoxyethylene (3) myristylether sulfate, higher fatty acid alkanolamide sulfate sodium, laurylphosphoric acid, sodium laurylphosphate, potassium cetylphosphate, diethanolamine cetylphosphate, polyoxyethylene oleylether phosphoric acid, polyoxyethylene laurylether phosphoric acid, sodium polyoxyethylene laurylether phosphate, polyoxyethylene cetylether phosphoric acid, sodium polyoxyethylene cetylether phosphate, polyoxyethylene stearylether phosphoric acid, polyoxyethylene oleylether phosphoric acid, sodium polyoxyethylene oleylether phosphate, polyoxyethylene alkylphenyl ether phosphoric acid, sodium polyoxyethylene alkylphenyl ether phosphate, triethanolamine polyoxyethylene alkylphenyl ether phosphate, polyoxyethylene octylether phosphoric acid, polyoxyethylene (10) alkyl (12, 13) ether phosphoric acid, polyoxyethylene alkyl (12-15) ether phosphoric acid, polyoxyethylene alkyl (12-16) ether phosphoric acid, triethanolamine polyoxyethylene laurylether phosphate and diethanolamine polyoxyethylene oleylether phosphate;

cationic surfactants such as dioctylamine, dimethylstearylamine, trilaurylamine, stearic acid diethylaminoethylamide, lauryltrimethylammonium chloride, cetyltrimethylammonium chloride, cetyltrimethylammonium bromide, cetyltrimethylammonium saccharin, stearyltrimethylammonium chloride, alkyl (20-22) trimethylammonium chloride, lauryltrimethylammonium bromide, alkyl (16, 18) trimethylammonium chloride, stearyltrimethylammonium bromide, stearyltrimethylammonium saccharin, alkyl (28) trimethylammonium chloride, di(polyoxyethylene)oleylmethylammonium chloride (2EO), dipolyoxyethylenestearylmethylammonium chloride, polyoxyethylene (1) polyoxypropylene (25) diethylmethylammonium chloride, tri(polyoxyethylene)stearylammonium chloride (5EO), distearyldimethylammonium chloride, dialkyl (12-15) dimethylammonium chloride, dialkyl (12-18) dimethylammonium chloride, dialkyl (14-18) dimethylammonium chloride, dicocoyldimethylammonium chloride, dicetyldimethylammonium chloride, isostearyllauryldimethylammonium chloride, benzalkonium chloride, myristyldimethylbenzylammonium chloride, lauryldimethyl(ethylbenzyl)ammonium chloride, stearyldimethylbenzylammonium chloride, laurylpyridinium chloride, cetylpyridinium chloride, lauroylcolaminoformylmethylpyridinium chloride, stearoylcolaminoformylmethylpyridinium chloride, alkylisoquinolium bromide, methylbenzethonium chloride and benzethonium chloride;

amphoteric surfactants such as 2-alkyl-N-carboxymethyl-N-hydroxyethyl imidazolinium betaine, alkyldiaminoethylglycine hydrochloride, lauryldiaminoethylglycine sodium, undecylhydroxyethylimidazolium betaine sodium, undecyl-N-carboxymethylimidazolium betaine, acyl-N-carboxyethyl-N-hydroxyethylethylenediamine disodium coconut fatty acid ester, acyl-N-carboxyethoxyethyl-N-carboxyethylethylenediamine disodium coconut fatty acid ester, acyl-N-carboxymethoxyethyl-N-carboxymethylethylenediamine disodium coconut fatty acid ester, sodium laurylaminopropionate, sodium laurylaminodipropionate, triethanolamine laurylaminopropionate, acyl-N-carboxyethyl-N-hydroxyethylethylenediamine sodium palm oil fatty acid ester, betaine lauryldimethylaminoacetate, betaine coconut oil alkyldimethylaminoacetate, betaine stearyldimethylaminoacetate, stearyldimethylbetainesodium, amidopropylbetaine coconut fatty acid ester, amidopropylbetaine palm oil fatty acid ester, lauric acid amide betaine propylacetate, ricinoleic acid amide propylbetaine, stearyldihydroxyethyl betaine and laurylhydroxysulfobetaine;

nonionic surfactants such as polyoxyethylene (10) alkyl (12, 13) ether, polyoxyethylene lauryl ether, polyoxyethylene cetyl ether, polyoxyethylene stearyl ether, polyoxyethylene oleyl ether, polyoxyethylene (3, 7, 12) alkyl (12-14) ether, polyoxyethylene tridecyl ether, polyoxyethylene myristyl ether, polyoxyethylene-sec-alkyl (14) ether, polyoxyethylene isocetyl ether, polyoxyethylene cetostearyl ether, polyoxyethylene (2, 10, 20) isostearyl ether, polyoxyethylene oleylcetyl ether, polyoxyethylene (20) arachyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene (1) polyoxypropylene (1, 2, 4, 8) cetyl ether, polyoxyethylene (5) polyoxypropylene (1, 2, 4, 8) cetyl ether, polyoxyethylene (10) polyoxypropylene (1, 2, 4, 8) cetyl ether, polyoxyethylene (20) polyoxypropylene (1, 2, 4, 8) cetyl ether, polyoxyethylene polyoxypropylene lauryl ether, polyoxyethylene (3) polyoxypropylene (34) stearyl ether, polyoxyethylene (4) polyoxypropylene (30) stearyl ether, polyoxyethylene (34) polyoxypropylene (23) stearyl ether, polyoxyethylene polyoxypropylene cetyl ether, polyoxyethylene polyoxypropylene decyltetradecyl ether, polyethylene glycol monolaurate, ethylene glycol monostearate, polyethylene glycol monostearate, polyethylene glycol monooleate, ethylene glycol fatty acid ester, self-emulsifiable ethylene glycol monostearate, diethylene glycol laurate, polyethylene glycol myristate, polyethylene glycol palmitate, diethylene glycol stearate, self-emulsifiable polyethylene glycol (2) monostearate, polyethylene glycol isostearate, ethylene glycol dioctanoate, diethylene glycol dilaurate, polyethylene glycol dilaurate, polyethylene glycol (150) dipalmitate, ethylene glycol distearate, diethylene glycol distearate, polyethylene glycol distearate, ethylene glycol dioleate, polyethylene glycol dioleate, polyethylene glycol diricinoleate, polyoxyethylene (20) sorbitan monolaurate, polyoxyethylene (20) sorbitan monopalmitate, polyoxyethylene (6) sorbitan monostearate, polyoxyethylene (20) sorbitan monostearate, polyoxyethylene (20) sorbitan tristearate, polyoxyethylene (6) sorbitan monooleate, polyoxyethylene (20) sorbitan monooleate, polyoxyethylene (20) sorbitan trioleate, sorbitan polyoxyethylene (20) coconut fatty acid ester, polyoxyethylene (10-80) sorbitan monolaurate, polyoxyethylene sorbitan tristearate, polyoxyethylene (20) sorbitan isostearate, polyoxyethylene (150) sorbitan tristearate, polyoxyethylene castor oil, polyoxyethylene hydrogenated castor oil, polyoxyethylene (10) hydrogenated castor oil, polyoxyethylene (20) hydrogenated castor oil, polyoxyethylene (40) hydrogenated castor oil, polyoxyethylene (50) hydrogenated castor oil, polyoxyethylene (60) hydrogenated castor oil, lipophilic glyceryl monostearate, lipophilic glyceryl monooleate, self-emulsifiable glyceryl monostearate, glyceryl coconut fatty acid ester, glyceryl laurate, glyceryl myristate, glyceryl isostearate, glyceryl ricinoleate, glyceryl monohydroxystearate, glyceryl oleate, glyceryl linoleate, glyceryl erucate, glyceryl behenate, wheat germ fatty acid glyceride, glyceryl safflower oil fatty acid ester, glyceryl hydrogenated soybean fatty acid ester, saturated fatty acid glyceride, glyceryl cotton seed oil fatty acid, monoisostearic acid glyceryl monomyristate, monotallow fatty acid glyceride, monoglyceryl lanolin fatty acid ester, glyceryl sesquioleate, glyceryl distearate, glyceryl diisostearate, glyceryl diarachidate, sorbitan monolaurate, sorbitan monopalmitate, sorbitan monostearate, sorbitan monoisostearate, sorbitan monooleate, sorbitan sesquistearate, sorbitan sesquioleate, sorbitan tristearate, sorbitan trioleate, sorbitan coconut fatty acid ester, sorbitan isostearate, sorbitan sesquiisostearate, sorbitan distearate, diglyceryl isopalmitate, poly(4-10) glyceryl monolaurate, poly (10) glyceryl monomyristate, poly(2-10) glyceryl monostearate, poly(2-10) glyceryl monoisostearate, poly(2-10) glyceryl monooleate, diglyceryl sesquioleate, poly(2-10) glyceryl diisostearate, poly(6-10) glyceryl distearate, diglyceryl triisostearate, poly (10) glyceryl tristearate, poly (10) glyceryl trioleate, poly (2) glyceryl tetraisostearate, decaglyceryl pentastearate, poly(6-10) glyceryl pentaoleate, poly (10) glyceryl heptastearate, decaglyceryl decastearate, poly (10) glyceryl decaoleate, condensed poly (6) glyceryl ricinoleate, sucrose fatty acid ester, sucrose coconut fatty acid ester, alkyl glucoside, coconut oil alkyldimethylamine oxide, lauryldimethylamine oxide, dihydroxyethyllauryldimethylamine oxide, stearyldimethylamine oxide, oleyldimethylamine oxide and polyoxyethylene coconut oil alkyldimethylamine oxide;

natural surfactants such as saponin, lecithin, soybean phospholipid, hydrogenated soybean phospholipid, soybean lysophospholipid, hydrogenated soybean lysophospholipid, egg yolk lecithin, hydrogenated egg yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid and mannosylerythritol lipid;

ultraviolet light absorbers, including paraminobenzoic acid derivatives such as paraminobenzoic acid, ethyl paraminobenzoate, glyceryl paraminobenzoate, amyl paradimethylaminobenzoate and 2-ethylhexyl paradimethylaminobenzoate, cinnamic acid derivatives such as benzyl cinnamate, diparamethoxy cinnamic acid glyceryl mono-2-ethylhexanoate, methyl 2,4-diisopropylcinnamate, ethyl 2,4-diisopropylcinnamate, potassium paramethoxycinnamate, sodium paramethoxycinnamate, isopropyl paramethoxycinnamate, 2-ethylhexyl paramethoxycinnamate, 2-ethoxyethyl paramethoxycinnamate and ethyl paraethoxycinnamate, urocanic acid derivatives such as urocanic acid and ethyl urocanate, benzophenone derivatives such as 2,4-dihydroxybenzophenone, 2,2',4,4'-tetrahydroxybenzophenone, 2-hydroxy-4-methoxy-5-sulfobenzophenonesodium, 2-hydroxy-4-methoxybenzophenone-5-sulfonic 2-hydroxy-4-methoxybenzophenone, 2,2'-dihydroxy-4,4'-dimethoxybenzophenone acid, and 2,2'-dihydroxy-4,4'-dimethoxy-5-sulfobenzophenonesodium, salicylic acid derivatives such as ethylene glycol salicylate, 2-ethylhexylsalicylate, phenyl salicylate, benzyl salicylate, p-tert-butylphenyl salicylate, homomethyl salicylate and 3,3,5-trimethylcyclohexyl 2-(2'-hydroxy-5'-methoxyphenyl) benzotriazole and 4-tert-butyl-4'-methoxybenzoylmethane;

powders and color materials such as kaolin, silicic anhydride, aluminum magnesium silicate, sericite, talc, boron nitride, mica, montmorillonite, hemp cellulose powder, wheat starch, silk powder, cornstarch, nitro dye, azo dye, nitroso dye, triphenylmethane dye, xanthene dye, quinoline dye, anthraquinone dye, indigo dye, pyrene dye, phthalocyanine dye, natural dyes including flavonoid, quinone, porphyrin, water-soluble annatto, squid ink powder, caramel, guaiazulene, gardenia blue, gardenia yellow, cochineal, shikonin, copper chlorophyllin sodium, paprika dye, safflower red, safflower yellow, laccaic acid and riboflavin butyrate, carbon black, yellow iron oxide, black iron oxide, red iron oxide, iron blue, ultramarine blue, zinc oxide, chromium oxide, titanium oxide, black titanium oxide, zirconium oxide, chromium hydroxide, alumina, magnesium oxide, barium sulfate, aluminum hydroxide, calcium carbonate, lithium cobalt titanate, manganese violet and pearl pigment;

plant extracts such as *angelica* extract, gambir extract, avocado extract, *hydrangea* extract, *gynostemma pentaphyllum* extract, *althea* extract, *arnica* extract, oil-soluble *arnica* extract, almond extract, *aloe* extract, *styrax* resin extract, *ginkgo* extract, nettle extract, orris extract, fennel extract, turmeric *curcuma* extract, rose fruit extract, *echinacea* leaf extract, *scutellaria* root extract, *phellodendron* bark extract, Japanese coptis rhizome extract, barley extract, okura extract, *hypericum* extract, oil-soluble *hypericum* extract, white nettle extract, oil-soluble white nettle extract, restharrow extract, watercress extract, orange flower water, persimmon tannin, *pueraria* root extract, Japanese valerian extract, cattail extract, chamomile extract, oil-soluble chamomile extract, chamomile water, oat extract, carrot extract, oil-soluble carrot extract, carrot oil, *artemisia capillaris* extract, *glycyrrhiza* extract, *glycyrrhiza* extracted powder, *glycyrrhiza* flavonoid, *cantharis* tincture, raspberry extract, kiwi extract, *cinchona* extract, cucumber extract, apricot kernel extract, quince seed extract, *gardenia* extract, *sasa albo-marginata* extract, *sophora* root extract, walnut shell extract, *clematis* extract, black sugar extract, *chlorella* extract, mulberry bark extract, cinnamon bark extract, *gentian* extract, *geranium* herb extract, black tea extract, *nuphar* extract, burdock root extract, oil-soluble burdock root extract, wheat germ extract, hydrolyzed wheat powder, rice bran extract, fermented rice bran extract, comfrey extract, *asiasarum* root extract, saffron extract, *saponaria* extract, oil-soluble *salvia* extract, *crataegus* fruit extract, *zanthoxylum* fruit extract, shiitake extract, shiitake mushroom extracted powder, *rehmannia* root extract, *lithospermum* root extract, oil-soluble *lithospermum* root extract, *perilla* herb extract, linden extract, oil-soluble linden extract, *filipendula* extract, peony root extract, job's tears extract, ginger extract, oil-soluble ginger extract, ginger tincture, *acorus calamus* rhizome extract, birch extract, oil-soluble birch extract, birch sap, honeysuckle extract, horsetail extract, oil-soluble horsetail extract, scordinin, *stevia* extract, ivy extract, *crataegus* extract, *sambucus* extract, juniper extract, yarrow extract, oil-soluble yarrow extract, peppermint extract, sage extract, oil-soluble sage extract, sage water, mallow extract, celery extract, *cnidium* rhizome extract, *cnidium* rhizome water, *swertia* herb extract, soy extract, jujube extract, thyme extract, green tea extract, tea leaf dry distillated solution, tee seed extract, clove extract, *citrus unshiu* peel extract, *camellia* extract, *centella* extract, oil-soluble walnut extract, duke extract, *terminalia* extract, Japanese angelica root extract, oil-soluble Japanese angelica root extract, Japanese angelica root water, *calendula* extract, oil-soluble *calendula* extract, soy milk powder, peach seed extract, bitter orange peel extract, *houttuynia* extract, tomato extract, *tormentilla* extract, natto extract, ginseng extract, oil-soluble ginseng extract, garlic extract, wild rose extract, oil-soluble wild rose extract, malt extract, malt root extract, *ophiopogon* tuber extract, parsley extract, barley leaf juice concentrate, peppermint distillate, witch hazel distillate, witch hazel extract, rose extract, pellitory extract, *isodonis* extract, loquat leaf extract, oil-soluble loquat leaf extract, coltsfoot extract, hoelen extract, butcher broom extract, butcher broom extracted powder, grape extract, grape leaf extract, grape water, hayflower extract, sponge gourd extract, sponge gourd solution, safflower extract, oil-soluble linden extract, linden water, *paeonia* extract, hop extract, oil-soluble hop extract, pine extract, *silybummarianum* fruit extract, horse chestnut extract, oil-soluble horse chestnut extract, mukurossi peel extract, balm mint extract, sweet clover extract, peach leaf extract, oil-soluble peach leaf extract, bean sprouts extract, corn flower extract, corn flower water, *eucalyptus* extract, *saxifraga* extract, lily extract, *coix* extract, oil-soluble *coix* extract, mugwort extract, Japanese mugwort water, lavender extract, lavender water, apple extract, *ganoderma* extract, lettuce extract, Chinese milk vetch extract, rose water, rosemary extract, oil-soluble rosemary extract, roman chamomile extract and burnet extract;

amino acids and peptides such as glycine, valine, leucine, isoleucine, serine, threonine, phenylalanine, thyrosin, tryptophan, cystine, cysteine, methionine, hydroxyproline, aspartic acid, asparagine, glutamic acid, glutamine, histidine, γ-aminobutyric acid, DL-pyrrolidonecarboxylic acid, ε-aminocaproic acid, hydrolyzed elastin, water-soluble elastin, hydrolyzed collagen, water-soluble collagen, casein, glutathione, wheat peptide and soybean peptide;

vitamins and vitamin affecters, including vitamin A such as retinol, retinal, retinoic acid, retinol acetate and retinol palmitate, carotenoids such as α-carotene, β-carotene, γ-carotene, δ-carotene, lycopene, zeaxanthin, cryptoxanthin, echinenone and astaxanthin, vitamin B1 such as thiamines, vitamin B2 such as riboflavin, vitamin B6 such as pyridoxine, pyridoxal and pyridoxamine, vitamin B12 such as cyanocobalamin, vitamin C such as folic acids, nicotinic acid, nicotinic acid amide, pantothenic acids, biotins, L-ascorbic acid, sodium L-ascorbate, L-ascorbyl stearate, L-ascorbyl palmitate, L-ascorbyl dipalmitate, L-ascorbyl tetraisopalmitate, disodium L-ascorbyl sulfate ester, L-ascorbyl magnesium, L-ascorbyl sodium phosphate, ascorbic acid-2-phosphate ester, and L-ascorbic acid-2-glucoside, vitamin D such as ergocalciferol and cholecalciferol, oil-soluble vitamin E such as d-α-tocopherol, DL-α-tocopherol, dl-α-tocopherol acetate, dl-α-tocopherol succinate, β-tocopherol, γ-tocopherol and d-δ-tocopherol, vitamin K, carnitine, ferulic acid, γ-oryzanol, α-lipoic acid and orotic acid;

antiseptics such as benzoic acid, sodium benzoate, undecylenic acid, salicylic acid, sorbic acid, potassium sorbate, dehydroacetic acid, sodium dehydroacetate, isobutyl paraoxybenzoate, isopropyl paraoxybenzoate, ethyl paraoxybenzoate, butyl paraoxybenzoate, propyl paraoxybenzoate, benzyl paraoxybenzoate, methyl paraoxybenzoate, methyl sodium paraoxybenzoate, phenoxyethanol, photosensitive agent(kankoh-so) No. 101, photosensitive agent(kankoh-so) No. 201 and photosensitive agent(kankoh-so) No. 401;

antioxidants such as butylhydroxyanisole, butylhydroxytoluene, propyl gallate, erythorbic acid, sodium erythorbate, parahydroxyanisole and octyl gallate;

sequestering agents such as trisodium ethylenediaminehydroxyethyltriacetate, edetic acid, disodium edetate, trisodium edetate, tetrasodium edetate, sodium citrate, gluconic acid, phytic acid, sodium polyphosphate and sodium metaphosphate;

moisturizers such as hyaluronic acid, sodium hyaluronate, sodium chondroitinsulfate, sodium lactate, sodium pyrrolidonecarboxylate, betaine, lactic acid bacteria culture solution, yeast extract and ceramide;

antiinflammatory agents such as glycyrrhizinic acid, trisodium glycyrrhizinate, dipotassium glycyrrhizinate, monoammonium glycyrrhizinate, β-glycyrrhetinic acid, glyceryl glycyrrhetinate, stearyl glycyrrhetinate, lysozyme chloride, hydrocortisone and allantoin;

pH adjusters such as sodium hydroxide, potassium hydroxide and triethanolamine;

salts such as sodium chloride, potassium chloride, magnesium chloride and sodium sulfate;

α-hydroxy acids such as citric acid, glycolic acid, tartaric acid and lactic acid;

whitening agents such as arbutin, α-arbutin and placental extract;

essential oils such as angelica oil, ylang ylang oil, elemi oil, matricaria oil, chamomile oil, cardamom oil, calamus oil, galbanum oil, camphor oil, carrot seed oil, clary sage oil, clove oil, cinnamon bark oil, coriander oil, cypress oil, sandalwood oil, cedarwood oil, citronella oil, cinnamon leaf oil, jasmine absolute, juniper berry oil, ginger extract, spearmint oil, sage oil, cedar oil, geranium oil, thyme oil, tea tree oil, nutmeg oil, niaouli oil, neroli oil, pine oil, basil oil, peppermint oil, patchouli oil, palmarosa oil, fennel oil, petitgrain oil, black pepper oil, frankincense oil, vetivert oil, peppermint oil, bergamot oil, benzoin oil, aniba rosaeodora oil, marjoram oil, myrrh oil, melissa oil, eucalyptus oil, ravensara oil, lavandin oil, lavender oil, lindane oil, rose oil, rosewood oil, rosemary oil and lovage oil;

terpenes such as pinene, terpinene, terpinolene, myrcene and longifolene;

perfumes and water.

In addition to the above-described components, conventional cosmetic materials may also be used as required. For instance, cosmetic materials described in the following references may be used while still achieving the effects of the present invention:

The Japanese Standards of Cosmetic Ingredients, The Second Edition Notes, edited by Society of Japanese Pharmacopoeia, 1984, (YAKUJI NIPPO LIMITED.);

The Japanese Cosmetic Ingredients Codex, supervised by Evaluation and Licensing Division, Pharmaceutical and Medical Safety Bureau, Ministry of Health, Labor and Welfare, 1993, (YAKUJI NIPPO LIMITED.);

Supplement to The Japanese Cosmetic Ingredients Codex, supervised by Evaluation and Licensing Division, Pharmaceutical and Medical Safety Bureau, Ministry of Health, Labor and Welfare, 1993, (YAKUJI NIPPO LIMITED.);

The Comprehensive Licensing Standards of Cosmetics by Category, supervised by Evaluation and Licensing Division, Pharmaceutical and Medical Safety Bureau, Ministry of Health, Labor and Welfare, 1993, (YAKUJI NIPPO LIMITED.);

Compounding Ingredients Codex of Cosmetics by Category, supervised by Evaluation and Licensing Division, Pharmaceutical and Medical Safety Bureau, Ministry of Health, Labor and Welfare, 1997, (YAKUJI NIPPO LIMITED.);

Dictionary of cosmetic materials, 1991, (Nikko Chemicals Co., Ltd.); and

Latest 300 Cosmetic Functional Materials, 2002, (CMC Publishing CO., LTD.).

The skin agent for external use according to the present invention is particularly suitable for use as a cosmetic agent. The advantages of the present invention are brought about by the enrichment of ubiquinone and ubiquinol surpassing the ubiquinone in antioxidant activity. Accordingly, it is apparent that the skin agent for external use of the present invention is effective in all applications of existing preparations containing ubiquinones as active ingredients. Known ubiquinone-containing skin agents for external use include antioxidant cosmetic agents, anti aging cosmetic agents, whitening cosmetic agents, skin roughness preventing cosmetic agents, anti wrinkle cosmetic agents, and cosmetic agents for preventing dullness and dark circle. The skin agent for external use according to the present invention may be used for the same purposes as these known cosmetic agents. The skin agent of the invention may be prepared according to a simple aqueous prescription. Moreover, the skin agent and the cosmetic agent of the present invention contain the active ingredients in high concentrations and are highly stable and effective.

The skin agent for external use and the cosmetic agent according to the present invention may be in any formulation or form as long as they are transdermally administered. More preferably, the skin agent for external use and the cosmetic agent are such that ubiquinone and ubiquinol are brought into contact with skin in the vicinity of a desired skin portion.

The formulations of the skin agent and cosmetic agent include skin milks, skin creams, foundation creams, massage creams, cleansing creams, shaving creams, cleansing foams, skin lotions, lotions, packs, lipsticks, rouges, eyeshadows, manicures, soaps, body shampoos, hand soaps, shampoos, conditioners, hair tonics, treatments, hair creams, hair sprays, hair restorers, hair-growth medicines, hair dyes, hair liquids, depilatories, dandruff inhibitors, toothpastes, denture adhesives, mouthwashes, permanent waving agents, curling agents, styling agents, ointments, cataplasms, tape agents, bath additives, antiperspirants and sun blockers. Any formulations applicable to skin may be used. The skin agent and the cosmetic agent according to the present invention can be used regardless of gender and age of users, and can be applied not only to humans but also to animals.

The skin agent and the cosmetic agent may be in any form, with examples including solids, liquids, semi-solids, gases, fine particles, granules, tablets, gels and foams. From the viewpoint that the present invention more effectively solves the background problem of difficult production of aqueous ubiquinone preparations, the formulations and forms preferably involve an aqueous medium. In this case, the water content in the skin agent or the cosmetic agent is preferably in the range of 0.01 to 99.99% by mass of the agent.

The concentration of the ubiquinone derivative in the skin agent or the cosmetic agent is not particularly limited and may be appropriately determined depending on desired effects of ubiquinone and ubiquinol, namely, desired antioxidant effects.

At the present time, the Ministry of Health, Labour and Welfare in Japan regulates that cosmetic agents should contain ubiquinone in an amount of not more than 0.03%. Even in such small amounts, the effectiveness of ubiquinone is recognized and the use thereof is widespread. In view of such background and the fact that the ubiquinone derivatives of the invention are highly capable of enriching the skin cells with ubiquinones and ubiquinols, the effects of ubiquinones and ubiquinols are substantially achieved when the concentration of the ubiquinone derivative is about 0.0005% or higher, preferably 0.001% or higher, more preferably 0.01% or higher. The maximum concentration of the ubiquinone derivative is not particularly limited. In order that the advantages of the invention are more effectively achieved, practical aqueous preparations will contain the ubiquinone derivatives in a maximum concentration of not more than 50%, preferably not more than 20%, more preferably not more than 10%. Formulations may be such that solid agents, concentrated agents or dispersion agents are prepared with a concentration of more than 50% and are adjusted to the above concentration when they are used.

EXAMPLES

While the present invention will be described below with reference to Examples, the present invention is not limited thereto. In Examples, % refers to % by mass unless otherwise mentioned.

Synthetic Example 1

Synthesis of Ubiquinol 30 g of ubiquinone (MW: 863.36) was dissolved in 300 ml of hexane. While the solution was stirred at room temperature, 300 ml of a 10% (w/v) sodium hyposulfite solution was poured to the solution. The mixture was stirred at room temperature for 2 hours. The mixture was all introduced into a separating funnel, and the hexane layer was collected. The remaining aqueous layer was then extracted twice each with 50 ml of hexane, and the extract was combined with the previously collected hexane layer. The hexane layer was washed six times each with 50 ml of a deaerated saturated saline solution, thereby obtaining a transparent hexane layer. After hexane was removed under a reduced pressure, nitrogen purging was performed for day and night, resulting in 29.5 g of a cream colored solid.

Synthetic Example 2

Synthesis of tetrapotassium ubiquinol-1,4-diphosphate 3 g of the solid obtained in Synthetic Example 1 was dissolved in 10 ml of pyridine. While the solution was in a freezing mixture (salt/ice) bath (−15° C.), a solution of phosphorus oxychloride (3.19 g) in pyridine (5 ml) was added dropwise to the solution. The mixture was stirred for 30 minutes with cooling, and was stirred at normal temperature for 2 hours. After the solvent was removed under a reduced pressure, the resultant oily matter was suspended in 300 ml of diethyl ether, and 150 ml of a saturated saline solution was added. The mixture was all introduced into a separating funnel, and was stirred by shaking. The mixture was then left at rest, and the ether layer was collected. The ether layer was washed by addition of 120 ml of dilute hydrochloric acid (concentrated hydrochloric acid:water=1:2), and the ether layer was dried over anhydrous magnesium sulfate. The solvent was removed under a reduced pressure, and 2.5 g of a yellow oily matter resulted. The oily matter was dissolved in 30 ml of methanol, and a solution of potassium hydroxide (0.547 g) in methanol (2 g) was added dropwise to the solution. The organic solvent was removed under a reduced pressure, and nitrogen purging was performed for day and night, resulting in 2.63 g of slightly yellow fine particles. The fine particles were identified to be tetrapotassium ubiquinol-1,4-diphosphate by NMR and mass spectrometry.

[NMR]
<$^1$H-NMR>
1.4-1.65 ppm (11H), 1.8-1.9 ppm (9H), 1.9-2.0 ppm (10H), 2.2-2.4 ppm (3H), 3.8-4.0 ppm (6H), 4.95-5.1 ppm (10H)
<$^{31}$P-NMR>
1.0-1.2 ppm
<Method>
Apparatus: Burker Advance-500
Solvent: $D_2O$
[Mass spectrometry]
FAB–MS (−): 1023 (=[M-H]$^-$)
<Method>
Direct introduction FAB-MS method
Apparatus: JEOL JMS-SX102A
FAB matrix: glycerin
Scanning range: m/Z 50-200

Example 1

Administration Test to Skin Cells

Normal human skin fibroblast cells NB1RGB (spared from RIKEN) were inoculated to a DMEM culture medium including 10% FBS on a 9 cm Petri dish such that the normal human skin fibroblast cells NB1RGB were approximately $1.0 \times 10^5$ in number per ml. The cells were cultured in a $CO_2$ incubator at 37° C. for 7 days to reach confluent while the culture medium was exchanged every 3 days. On the seventh day, the culture medium was exchanged to a DMEM culture medium including 0.03% of tetrapotassium ubiquinol-1,4-diphosphate prepared in Synthetic Example 2, and the cells were further cultured for 3 days under the same conditions. After the culture, the cells were cleaned three times on the Petri dish each with 10 ml of PBS(−), and were released and recovered using trypsin/EDTA. The cells were then resuspended in 1 ml of PBS(−), and were quickly broken with a homogenizer. Insoluble matters were removed by centrifugal separation at 10000 rpm for 10 minutes, and 10 μl of the supernatant was subjected to HPLC. The remainder was combined with an equivalent amount of hexane, and these were sufficiently mixed together to give a turbid liquid. The turbid liquid was subjected to centrifugal separation at 10000 rpm for 3 minutes, and the resultant supernatant hexane layer was analyzed by HPLC.

<HPLC condition>
Column: Shodex F-511A (manufactured by Showa Denko K.K)
Column temperature: 40° C.
Eluent: methanol/water/phosphoric acid=1000/5/1
Rate of flow: 1.0 ml/min
Detection: photodiode array 210 nm-370 nm In the HPLC analysis, ubiquinone used in Synthetic Example 1 and ubiquinol immediately after synthesized in Synthetic Example 1 were used as references. The HPLC of the supernatant including the pulverized cells provided an absorption spectrum (210-370 nm) that showed retention times and peaks assigned to ubiquinol-1,4-diphosphoric acid and ubiquinol. The HPLC of the n-hexane extract provided an absorption spectrum (210-370 nm) that showed retention times and peaks assigned to ubiquinol and ubiquinone. Based on the volume of the cells that were recovered, the concentrations of these compounds in the cells were estimated as shown in Table 1.

Comparative Example 1

The procedures and analysis of Example 1 were repeated, except that the cells were cultured without addition of tetrapotassium ubiquinol-1,4-diphosphate. The results are shown in table 1.

Comparative Example 2

To a DMEM culture medium including 10% FBS, reagent ubiquinone was added in an amount corresponding to 0.03%. The mixture was stirred with a stirrer at room temperature for 6 hours. The mixture was filtered through a 0.02 □m filter, and a ubiquinone-containing culture medium was prepared. The ubiquinone concentration in the culture medium was determined to be 0.007% by HPLC under the above-mentioned conditions using ubiquinone used in Synthetic Example 1 as reference. The ubiquinone concentration was not increased by further stirring, and this concentration was probably the maximum with the above culture medium at room temperature.

The procedures and analysis of Example 1 were repeated, except that the above ubiquinone-containing culture medium was used in place of the DMEM culture medium including 0.03% of tetrapotassium ubiquinol-1,4-diphosphate. The results are shown in table 1.

TABLE 1

| | Concentration in cells after culture (µg/ml) | | |
|---|---|---|---|
| | Ubiquinol-1,4-diphosphoric acid | Ubiquinone | Ubiquinol |
| Example 1 (tetrapotassium ubiquinol-1,4-diphosphate | 241 | 14 | 78 |
| Comparative Example 1 (none) | Not detected | Not detected | Not detected |
| Comparative Example 2 (ubiquinone) | Not detected | 2 | Not detected |

Example 2

Preparation of Cosmetic Liquids

Cosmetic liquids were prepared based on the following prescription examples 1 to 4. In the prescription examples 1 to 4, the total of the components of A and B was 100%.

Prescription Example 1

A

Dipotassium glycyrrhizate: 0.2%
Tetrapotassium ubiquinol-1,4-diphosphate: 1.0%
Citric acid: 0.1%
Sodium citrate: 0.3%
Purified water: balance

B

Polyoxyethylene sorbitol tetraoleate: 0.9%
Sorbitan monooleate: 0.1%
Olive oil: 0.1%
Dipropylene glycol: 5.0%
Methylparaben: 0.1%
Ethanol: 10.0%

Prescription Example 2

A

Sodium citrate: 0.1%
Glycerin: 8.0%
Sodium pyrrolidone carboxylate: 1.0%
Trehalose: 0.03%
1,3-butylene glycol: 5.0%
Tetrapotassium ubiquinol-1,4-diphosphate: 0.3%
Purified water: balance

B

Polyoxyethylene polyoxypropylene decyltetradecyl ether: 0.6%
Methylparaben: 0.1%
Ethanol: 10.0%

Prescription Example 3

A

Polyvinyl alcohol: 0.1%
Carboxyvinyl polymer: 0.2%
Glycerin: 3.0%
Trisodium edentate: 0.1%
Sodium hydroxide: 0.05%
2-amino-2-methyl-1-propanol: 0.06%
Caffeine: 0.1%
Tetrapotassium ubiquinol-1,4-diphosphate: 0.5%
Purified water: balance

B

Ethanol: 20.0%
Polyoxyethylene oleyl ether: 0.3%
Methylparaben: 0.1%
Menthol: 0.1%

In the prescription examples 1 to 3, the components of A were mixed with each other and the components of B were mixed with each other in advance. The mixtures were then heated at 50° C. to dissolution. The mixture B was added to the mixture A little by little while the mixture A was stirred, and the mixture B was dissolved in the mixture A. The resultant mixture was cooled with stirring. When the temperature reached 30° C., the stirring was stopped. The liquid was then allowed to stand. The cosmetic liquids were thus prepared.

Prescription Example 4

A 1,3-butylene glycol: 5.02%
Cholesteryl/behenyl/octyldodecyl lauroyl glutamate: 0.5%
Trehalose: 0.03%
Trioctanoin: 0.03%
PEG-58 hydrogenated castor oil isostearate: 1.5%
PEG-60 hydrogenated castor oil: 0.5%
Methylparaben: 0.2%
Propylparaben: 0.01%
Tocopherol: 0.05%

B

Tetrapotassium ubiquinol-1,4-diphosphate: 0.5%
Sodium malate: 0.1%
Malic acid: suitable amount
Purified water: balance The components of A were mixed with each other and the components of B were mixed with each other in advance. The mixtures were then heated at 60° C. to dissolution. The mixture B was added to the mixture A while the mixture A was stirred. The resultant mixture was cooled to give a uniform cosmetic liquid.

Example 3

Test of Accelerating the Regeneration of Stratum Corneum

A cosmetic liquid A containing 1.0% of tetrapotassium ubiquinol-1,4-diphosphate was prepared based on the prescription example 1 of Example 2. Cosmetic liquids B and C were prepared based on the prescription example 1 of Example 2 except that the tetrapotassium ubiquinol-1,4-diphosphate was replaced by a maximum soluble amount of ubiquinone or ubiquinol, respectively.

Specifically, ubiquinone or ubiquinol was added in an amount corresponding to 1.0%. The resultant suspension was filtered through 1-μm filter paper, and thereby insolubles were removed. The cosmetic liquids B and C were thus prepared.

The final concentrations of ubiquinone and ubiquinol in the cosmetic liquids B and C were measured by HPLC similarly to Example 1, resulting in 0.011% and 0.023%, respectively.

A cosmetic liquid D was prepared based on the prescription example 1 of Example 2, except that tetrapotassium ubiquinol-1,4-diphosphate was not used.

The cosmetic liquids A to D were each applied to the inside of the arm of respective five subjects, two times a day (morning and evening) for 21 days. On the twenty second day, an ointment which was based on white vaseline and contained 5% by weight of dansyl chloride was applied to the arm. The arm with the ointment was prevented from exposure to the outside air for 24 hours, and dansyl chloride was allowed to penetrate the skin and bond to the stratum corneum. Thereafter, the identical cosmetic liquids were applied to the tested portion of the arm two times a day (morning and evening), and the fluorescence of dansyl chloride was measured everyday until the intensity was 50% of the initial intensity (after 24 hours after the dansyl chloride ointment was applied). The average number of days was obtained from the five subjects, and the acceleration of the regeneration of skin stratum corneum was evaluated.

The results are shown in Table 2. In the subjects given the cosmetic liquid A, the half-value period of fluorescence intensity was significantly short. This result proved that the regeneration of stratum corneum had been accelerated.

TABLE 2

|  | Half-value period (Days) | Standard error (Days) |
|---|---|---|
| Cosmetic liquid A (Tetrapotassium ubiquinol-1,4-diphosphate) | 6.2 | ±1.0 |
| Cosmetic liquid B (Ubiquinone) | 8.1 | ±0.8 |
| Cosmetic liquid C (Ubiquinol) | 8.5 | ±0.7 |
| Cosmetic liquid D (None) | 8.5 | ±1.2 |

Example 4

Test of Improvement of Skin Roughness

The cosmetic liquids A to D prepared in Example 3 were each applied to respective five subjects who were in their thirties and forties and suffered skin roughness in limb. Specifically, the cosmetic liquids A to D were each applied in an amount of about 0.5 g to a left limb portion of each subject, two times a day (morning and evening) for 4 weeks. The skin condition before and after the treatment was evaluated based on the criteria shown in Table 3. The right limb was not given any cosmetic liquids and was used as control.

The treated left limb was compared with the untreated right limb, and the improvement of skin dryness was evaluated based on the criteria shown in Table 3. When the skin dryness was improved by two or more stages (for example, +→−, or ++→±), the evaluation was "effective". When the skin dryness was improved by one stage, the evaluation was "slightly effective". When there was no improvement, the evaluation was "ineffective". The number of the subjects who answered "effective" and "slightly effective" is set forth in Table 4. In the subjects given the cosmetic liquid A, skin roughness was significantly improved.

TABLE 3

| Class | Evaluation |
|---|---|
| − | Normal |
| ± | Slightly dry and no scales |
| + | Dry and slight degree of scales |
| ++ | Dry and intermediate degree of scales |
| +++ | Dry and severe degree of scales |

TABLE 4

|  | Improved roughness (subject(s)/5 subjects) |
|---|---|
| Cosmetic liquid A (Tetrapotassium ubiquinol-1,4-diphosphate) | 5 |
| Cosmetic liquid B (Ubiquinone) | 2 |
| Cosmetic liquid C (Ubiquinol) | 1 |
| Cosmetic liquid D (None) | 1 |

Example 5

Test of Improvement of Stratum Corneum Condition (Improved Resistance of Stratum Corneum Cells to Detachment)

Before and after the test of skin roughness improvement in Example 4, a mending tape (manufactured by NICHIBAN CO., LTD.) was applied to and peeled from the skin portion that was tested. The stratum corneum cells attached to the tape were observed with a microscope. The detachment of stratum corneum cells was classified based on the criteria shown in Table 5, and the improvement of stratum corneum condition was evaluated.

When the comparison of the tested skin portion and the control confirmed improvement by two or more grades, the evaluation was "effective". The evaluations were "slightly effective" and "ineffective" when the comparison confirmed improvement by one grade or no improvement, respectively. The number of the subjects who answered "effective" and "slightly effective" is set forth in Table 6. In the subjects given the cosmetic liquid A, skin roughness was significantly improved.

TABLE 5

| Class | Evaluation |
|---|---|
| 1 | There were no scales. |
| 2 | Scales scattered. |
| 3 | Small and medium scales were remarkable. |
| 4 | Large scales were remarkable. |

TABLE 6

|  | Improved roughness (subject(s)/5 subjects) |
| --- | --- |
| Cosmetic liquid A (Tetrapotassium ubiquinol-1,4-diphosphate) | 5 |
| Cosmetic liquid B (Ubiquinone) | 1 |
| Cosmetic liquid C (Ubiquinol) | 1 |
| Cosmetic liquid D (None) | 0 |

Example 6

Sensory Test

The cosmetic liquids A to D prepared in Example 3 were each applied to respective five female subjects who were in their thirties and forties and suffered skin troubles such as skin roughness, wrinkles and dry skin, two times a day (morning and evening) for 2 months. The cosmetic liquids were tested with respect to typical sensory indexes of anti-aging effects: skin moisture, skin smoothness and skin fitness. The number of the subjects who realized moist skin, smooth skin and skin fitness is set forth in Table 7. In the subjects given the cosmetic liquid A, significant anti-aging effects were proved.

TABLE 7

|  | Skin moisture (subject(s)) | Skin smoothness (subject(s)) | Skin fitness (subject(s)) |
| --- | --- | --- | --- |
| Cosmetic liquid A (Tetrapotassium ubiquinol-1,4-diphosphate) | 4 | 5 | 4 |
| Cosmetic liquid B (Ubiquinone) | 1 | 1 | 1 |
| Cosmetic liquid C (Ubiquinol) | 2 | 1 | 1 |
| Cosmetic liquid D (None) | 2 | 1 | 0 |

Example 7

Test of Radical Scavenging Ability

Radical fluorescence detecting agent H2-DCFDA (manufactured by Invitrogen Corporation) was dissolved in a small amount of ethanol. The resultant solution was added to a 10 mM aqueous sodium hydroxide solution such that the concentration of the agent was 1 mM. The radical fluorescence detecting agent was hydrolyzed in the dark at room temperature for 60 minutes and was activated. The liquid was diluted with Dulbecco's phosphate buffered saline (PBS) to give a diluted liquid with a final concentration of 0.01 mM.

To 0.1 mL of the diluted liquid was added a 1% potassium ubiquinol-1,4-diphosphate solution that had been prepared by dissolving potassium ubiquinol-1,4-diphosphate in a 1% aqueous surfactant solution (surfactant: EMALEX HC-40 manufactured by Nihon Emulsion Co., Ltd.). The resultant mixture had a final concentration of ubiquinone derivative of 0.006%. The mixture thus prepared was used as a test liquid.

A test liquid having a final ubiquinone concentration of 0.006% was prepared in the same manner using ubiquinone.

A test liquid was prepared as described above except that the ubiquinone solution was replaced by the same volume of distilled water. This test liquid was used as a negative control.

To each of these three test liquids was added 0.01 mL of a 3 mM solution of water soluble radical generator 2,2'-azobis (2-aminopropane)dihydrochloride (AAPH). The mixture was heated to 37° C. After 30 minutes after the addition, the fluorescence intensity at an excitation wavelength of 495 nm and a fluorescence wavelength of 525 nm of the respective liquids was measured. The fluorescence suppression was obtained as radical scavenging ability of ubiquinone and potassium ubiquinol-1,4-diphosphate. The results are shown in Table 8.

TABLE 8

|  | Distilled water | Ubiquinone | Potassium ubiquinol-1,4-diphosphate |
| --- | --- | --- | --- |
| Fluorescence intensity (Ex 495/Em 525 nm: relative value) | 22723 | 13315 | 5001 |
| Radical scavenging ability (Fluorescence suppression (%)) | — | 41 | 78 |

Example 8

Preparation of Emulsions

Emulsions were prepared based on the following prescription examples 5 to 7. In the prescription examples 5 and 6, the total of the components of A and B was 100%. In the prescription example 7, the total of the components of A, B and C was 100%.

Prescription Example 5

A

Squalane: 10.0%
Polyoxyethylene glyceryl isostearate: 3.5%
Polyoxyethylene hydrogenated castor oil triisostearate: 6.5%
Pyroglutamic acid polyoxyethylene hydrogenated castor oil isostearate: 12.0%
Methylparaben: 0.1%

B

Tetrapotassium ubiquinol-1,4-diphosphate: 1.0%
Purified water: balance

The components of A were mixed with each other and the components of B were mixed with each other. The mixtures A and B were then heated at 70° C. and 50° C., respectively, to dissolution. The mixture B was added to the mixture A little by little while the mixture A was stirred, and an emulsion was prepared. The emulsion was cooled with stirring and diluted ten times with purified water.

Prescription Example 6

A

Fluid paraffin: 10.6%
Isopropyl myristate: 0.6%

Oleyl alcohol: 1.2%
Polyoxyethylene stearyl ether: 3.4%
PEG distearate: 1.9%
Polyoxyethylene polyoxypropylene tetradecyl ether: 0.4%

B

Tetrapotassium ubiquinol-1,4-diphosphate: 0.3%
Sodium stearoyl glutamate: 0.1%
Propylene glycol: 1.4%
Methylparaben: 0.1%
PEG-400: 0.2%
Purified water: balance The components of A were mixed with each other and the components of B were mixed with each other in advance. The mixtures A and B were then heated at 70° C. and 75° C., respectively, to dissolution. The mixture A was added to the mixture B little by little while the mixture B was stirred, and an emulsion was prepared. The emulsion was cooled with stirring.

Prescription Example 7

A

Polyoxyethylene sorbitan monostearate: 1.0%
Polyoxyethylene sorbitol tetraoleate: 0.5%
Sorbitan monostearate: 1.0%
Stearic acid: 0.5%
Behenyl alcohol: 0.5%
Bees wax: 0.5%
Squalane: 10.0%
Glyceryl tri-2-ethylhexanoate: 10.0%
Decaglyceryl decaoleate: 3.0% 1,3-butylene glycol: 7.0%
Methylparaben: 0.1%

B

Tetrapotassium ubiquinol-1,4-diphosphate: 0.3%
Xanthan gum: 0.04%
Carboxyvinyl polymer: 0.08%
Purified water: balance

C

Triethanolamine: 0.05%
Purified water: 4.95%

The components of A were mixed with each other, the components of B were mixed with each other, and the components of C were mixed with each other. The mixtures A and B were heated at 80° C. to dissolution. The mixture C was homogenized at room temperature. The mixture B was added to the mixture A while the mixture A was stirred, and an emulsion was prepared. The mixture C was then added to the emulsion. The mixture was cooled with stirring and became an emulsion-like state when the temperature was about 40° C. The emulsion-like composition was cooled to room temperature.

Example 9

Preparation of Gels

Gels were prepared based on the following prescription examples 8 to 13. In the prescription example 8, the total of the components of A and B was 100%. In the prescription example 9, the total of the components of A to E was 100%. In the prescription examples 10 to 13, the total of the components of A to C was 100%.

Prescription Example 8

A

Agar: 2.0%
Xanthan gum: 0.2%
Caffeine: 0.1%
Purified water: 50.0%
Tetrapotassium ubiquinol-1,4-diphosphate: 0.8%

B

Glycerin: 7.0%
PEG-1500: 8.0%
Methylparaben: 0.1%
Purified water: balance

The components of A were mixed with each other and the components of B were mixed with each other. The mixtures A and B were then heated at 90° C. and 50° C., respectively, to dispersion. The mixture A was cooled to 50° C. The mixture B was added to the mixture A while the mixture A was stirred. The mixture was cooled to not more than 30° C. with stirring and was gelled. When the mixture was sufficiently hard, the gel was broken using a disperser into a microgel. The microgel was deaerated to give a uniform gel (semi-transparent gel).

Prescription Example 9

A

Carboxyvinyl polymer: 0.35%
Purified water: 50.0%

B

Sodium hydroxide: 0.1%
Purified water: 10.0%

C

Sodium hyaluronate 1% aqueous solution: 6.0%
Tetrapotassium ubiquinol-1,4-diphosphate: 1.0%
Purified water: balance

D

Polyoxyethylene polyoxypropylene tetradecyl ether: 0.3%
Ethanol: 5.0%
Methylparaben: 0.1%
2-hexyldecanoic L-carnitine hydrochloride: 0.3%

E

Perfluoropolyether: 0.2%

The components of A were mixed with each other, the components of B were mixed with each other, the components of C were mixed with each other, and the components of D were mixed with each other. The mixtures A and B formed solutions at normal temperature. The mixtures C and D were heated at 50° C. and 40° C., respectively, to dissolution. The mixture B was added to the mixture A while the mixture A was stirred, and a gel was obtained. The mixtures C and D, and the component E were then added to the gel. They were mixed together by stirring. Subsequently, the mixture was deaerated to give a uniform gel (semi-transparent gel).

Prescription Example 10

A

Carboxyvinyl polymer: 0.5%
Purified water: 40.0%

B

Potassium hydroxide: 0.1%
Purified water: 10.0%

C

Dipropylene glycol: 10.0%
Methylparaben: 0.1%
Dipotassium glycyrrhizate: 0.05%
Hydrolyzed collagen: 0.05%
Tetrapotassium ubiquinol-1,4-diphosphate: 0.5%
Purified water: balance The components of A were mixed with each other, the components of B were mixed with each other, and the components of C were mixed with each other. The mixtures A and B formed solutions at normal temperature. The mixture C was heated at 50° C. to dissolution. The mixture B was then added to the mixture A while the mixture A was stirred, and a gel was formed. The mixture C was then added to the gel. They were mixed together by stirring. Subsequently, the mixture was deaerated to give a uniform gel (semi-transparent gel).

Prescription Example 11

A

Glycerin: 10.0%
1,3-butylene glycol: 6.0%
Dimethicone: 2.0%
PEG-60 hydrogenated castor oil: 0.6%
Laureth-2: 0.1%
Laureth-21: 0.1%
Methylparaben: 0.26%
Propylparaben: 0.1%
Ethylparaben: 0.1%
Phenoxyethanol: 0.1%
Tocopherol acetate: 0.1%
Chitosan succinamide: 0.01%
Yeast extract: 0.1%
Ethanol: 0.01%
Perfume: 0.01%

B

Tetrapotassium ubiquinol-1,4-diphosphate: 1.0%
Carboxyvinyl polymer: 0.5%
Urea: 0.02%
Glucosamine hydrochloride: 0.01%
Disodium edentate: 0.01%
Purified water: 50.0%

C

Arginine: 0.63%
Purified water: balance

The components of A were mixed with each other, the components of B were mixed with each other, and the components of C were mixed with each other. The mixture A was heated at 60° C. to dissolution. The mixtures B and C formed solutions at normal temperature. The mixture B was added to the mixture A while the mixture A was stirred, and a gel was formed. The mixture C was then added to the gel. They were mixed together by stirring. Subsequently, the mixture was cooled to room temperature to give a uniform gel (semi-transparent gel).

Prescription Example 12

A

Glycerin: 50.0%
Tourmaline: 5.0%
Olive oil: 1.0%
PEG-12: 28.0%
PEG-75: 7.5%
Polyglyceryl laurate: 1.0%
Ethanol: 0.49%
Acrylic acid/C10-30 acrylate copolymer: 0.11%
Methylparaben: 0.11%
Propylparaben: 0.02%
*Ginkgo biloba* extract: 0.02%
Green tea extract: 0.02%
*Aesculus hippocastanum* extract: 0.02%
Algae extract: 0.02%

B

Carboxyvinyl polymer: 0.07%
Purified water: 3.0%

C

Sodium hydroxide: 0.01%
Tetrapotassium ubiquinol-1,4-diphosphate: 1.0%
Purified water: balance The components of A were mixed with each other, the components of B were mixed with each other, and the components of C were mixed with each other. The mixture A was heated at 60° C. to dissolution. The mixtures B and C formed solutions at normal temperature. The mixture B was then added to the mixture A while the mixture A was stirred, and a gel was formed. The mixture C was added to the gel. They were mixed together by stirring. Subsequently, the mixture was cooled to room temperature to give a uniform gel (semi-transparent gel).

Prescription Example 13

A

Decamethylcyclopentasiloxane: 20.0%
Potassium ascorbate: 3.0%
Tetrapotassium ubiquinol-1,4-diphosphate: 0.1%

B

Squalane: 50.0%
Light fluid isoparaffin: balance
Dextrin palmitate: 8.0%

C

Octyl methoxycinnamate: 1.0%
Phenoxyethanol: 0.5%
α-tocopherol: 0.1%

The components of A, the components of B, and the components of C were weighed. The components of A were kneaded with a bead mill at normal temperature. The components of B were heated until they were dissolved uniformly. The components of C were dissolved at normal temperature. The mixture C was added to the mixture B while the mixture B was stirred, and they formed a uniform mixture. The mixture was then cooled to room temperature with stirring. Subsequently, the mixture A was added thereto, and the mixture was sufficiently stirred to give a uniform gel (semi-transparent gel).

Example 10

Preparation of Cosmetic Liquids

Cosmetic liquids were prepared based on the following prescription examples 14 to 16. In the prescription example 14, the total of the components of A to D was 100%. In the prescription example 15, the total of the components of A and B was 100%. In the prescription example 16, the total of the components of A, B and C was 100%.

Prescription Example 14

A

Xanthan gum: 0.4%
Hydroxyethyl cellulose: 0.1%
Carboxyvinyl polymer: 0.1%
1,3-butylene glycol: 5.0%
Tetrapotassium ubiquinol-1,4-diphosphate: 0.3%
Purified water: 50.0%

B

Potassium hydroxide (1% aqueous solution): 2.5%
Purified water: 10.0%

C

Caffeine: 1.0%
Purified water: balance

D

Methylparaben: 0.1%
Ethanol: 3.0%

The components of A were mixed with each other, the components of B were mixed with each other, the components of C were mixed with each other, and the components of D were mixed with each other. The mixtures A, B and D formed solutions at normal temperature. The mixture C was heated at 50° C. to dissolution. The mixture B was added to the mixture A while the mixture A was stirred, and a viscous liquid was formed. The mixtures C and D were then added to the liquid. They were mixed together by stirring to give a uniform liquid (cosmetic liquid).

Prescription Example 15

A 1,3-butylene glycol: 10.0%
Glycerin: 5.0%
Sodium hyaluronate: 0.2%
Xanthan gum: 0.2%
Dipotassium glycyrrhizate: 0.02%
Tetrapotassium ubiquinol-1,4-diphosphate: 0.3%
Purified water: balance

B

Ethanol: 3.0%
Hydrogenated lecithin: 0.5%
Trioctanoin: 0.3%
Diphenyl dimethicone: 0.2%
Methylparaben: 0.22%
Phenoxyethanol: 0.08%
PEG-50 hydrogenated castor oil: 0.1%
PEG-60 hydrogenated castor oil: 0.1%
α-tocopherol: 0.01%
Polyglyceryl-10 myristate: 0.05%

The components of A were mixed with each other, and the components of B were mixed with each other. The mixtures A and B were heated at 50° C. to dissolution. The mixture B was added to the mixture A while the mixture A is stirred. The mixture was cooled with stirring to give a uniform liquid (cosmetic liquid).

Prescription Example 16

A

Xanthan gum: 0.4%
Hydroxyethyl cellulose: 0.4%
1,3-butylene glycol: 3.0%
Glycerin: 3.0%
Methylparaben: 0.1%
Purified water: balance

B

Tetrapotassium ubiquinol-1,4-diphosphate: 2.0%
1,2-hexanediol: 4.0%
Purified water: 50.0%

C

Ascorbic acid-2-magnesium phosphate: 1.5%
Ascorbic acid-2-sodium phosphate: 1.5%
Sodium citrate: 0.5%
Tetrasodium edentate: 0.1%
Purified water: 9.4%

The components of A were mixed with each other, the components of B were mixed with each other, and the components of C were mixed with each other. The mixtures A and C formed solutions at normal temperature. The mixture B was heated at 50° C. to dissolution. The mixture B was then added to the mixture A while the mixture A was stirred, and a viscous liquid was formed. The mixture C was added to the liquid. They were mixed together by stirring to give a uniform liquid (cosmetic liquid).

Example 11

Preparation of Cream

A cream was prepared based on the following prescription example 17. In the prescription example 17, the total of the components of A and B was 100%.

Prescription Example 17

A

Hydrogenated rapeseed oil alcohol: 4.2%
Isononyl isononanoate: 6.0%

Squalane: 9.6%
Octyldodecyl myristate: 4.8%
Polyglyceryl monostearate: 2.0%
Glyceryl stearate: 1.0%
Propylparaben: 0.05%
Xanthan gum: 0.1%
α-tocopherol: 0.5%

B 1,3-butylene glycol: 4.8%
Glycerin: 4.8%
Tetrapotassium ubiquinol-1,4-diphosphate: 0.8%
Ascorbic acid-2-phosphoric acid-6-sodium palmitate: 1.0%
Methylparaben: 0.1%
Purified water: balance The components of A were mixed with each other, and the components of B were mixed with each other. The mixtures A and B were heated at 85° C. to dissolution. The mixture B was added to the mixture A while the mixture A was stirred, and an emulsion was formed. The emulsion was cooled with stirring. The stirring was stopped when the temperature reached about 40° C., and the product was deaerated to give a cream.

Example 12

Preparation of Sheet Packs

Sheet packs were prepared based on the following prescription examples 18 and 19. In the prescription examples 18 and 19, the total of the components of A and B was 100%.

Prescription Example 18

A

Glycerin: 30.0%
Alumina magnesium hydroxide: 1.0%

B

Diisopropanolamine: 1.0%
Sodium polyacrylate: 2.0%
Acrylic acid/sodium acrylate (50/50 (molar ratio)) copolymer: 2.0%
Tetrapotassium ubiquinol-1,4-diphosphate: 0.3%
Ascorbic acid-2-magnesium phosphate: 3.0%
Purified water: balance Prescription Example 19

A 1,3-butylene glycol: 30.0%
Coprecipitation substance of aluminum hydroxide gel and sodium hydrogen carbonate: 0.05%

B

Sodium acrylate/acrylic acid (70/30 (molar ratio)) copolymer: 1.0%
Polyacrylic acid: 1.0%
N-vinyl acetamide/sodium acrylate (9/1 (weight ratio)) copolymer: 3.0%
Aluminum lactate: 0.05%
Ammonia 10% aqueous solution: 0.01%
Tetrapotassium ubiquinol-1,4-diphosphate: 0.3%
Purified water: balance In each of the above prescription examples 18 and 19, the components of A were mixed with each other, and the components of B were mixed with each other. The mixture A formed a dispersion at normal temperature. The mixture B was heated at 50° C. to dissolution. The mixture B was cooled to room temperature with stirring. The mixture A was added to the mixture B little by little with stirring. The resultant sol was spread on a liner made of polypropylene at clearances of 0.5 mm by using a knife coater. A nonwoven fabric was then attached on the sol. The unit was placed in an aluminum laminate bag and the bag was heat-sealed. The sol was then aged for 3 days. A sheet pack was thus prepared.

Example 13

Preparation of Pack Agent

A pack agent (peel off pack) was prepared based on the following prescription example 20. In the prescription example 20, the total of the components of A and B was 100%.

Prescription Example 20

A

Polyvinyl alcohol: 13.0%
Carrageenan: 0.5%
Tetrapotassium ubiquinol-1,4-diphosphate: 1.0%
Purified water: balance

B 1,3-butylene glycol: 3.0%
Methylparaben: 0.1%
Ethanol: 8.0%

The components of A were mixed with each other, and the components of B were mixed with each other. The mixture A was heated at 50° C. and was swollen. The mixture B formed a solution at normal temperature. The mixture B was added to the mixture A little by little while the mixture A was stirred. Subsequently, the mixture was cooled with stirring. The stirring was stopped when the temperature was about 30° C. The mixture was allowed to stand to give a peel off pack.

Example 14

Preparation of Bath Additives

Bath additives were prepared based on the following prescription examples 21 and 22. In the prescription examples 21 and 22, the total of the components was 100%.

Prescription Example 21

Polyoxyethylene sorbitol tetraoleate: 14.0%
Polyoxyethylene oleyl ether: 3.0%
Sorbitan sesquioleate: 3.0%
Squalane: 10.0%
Jojoba oil: 20.0%
Avocado oil: 5.0%
Propylparaben: 0.1%
Tetrapotassium ubiquinol-1,4-diphosphate: 1.0%
Fluid paraffin: balance

Prescription Example 22

Sodium hydrogen carbonate: 35.5%
Citric acid: 37.1%
Polyethylene glycol: 2.1%
Magnesium oxide: 1.1%
α-tocopherol: 1.2%
Ascorbic acid-2-sodium phosphate: 1.5%
Ascorbic acid-2-glucoside: 1.5%
Tetrapotassium ubiquinol-1,4-diphosphate: 1.0%

In each of the above prescription examples 21 and 22, all the components were stirred at normal temperature until they were homogeneous.

Example 15

Preparation of Facial Cleansers

Facial cleansers were prepared based on the following prescription examples 23 and 24. In the prescription example 23, the total of the components of A to C was 100%. In the prescription example 24, the total of the components of A and B was 100%.

Prescription Example 23

A

Myristic acid: 15.0%
Palmitic acid: 5.0%
Stearic acid: 3.0%
Bees wax: 3.0%
PEG-6000: 2.0%
Ethylene glycol distearate: 2.0%
Coconut oil fatty acid diethanolamide: 3.0%
Concentrated glycerin: 15.0%

B

Potassium hydroxide: 5.5%
Purified water: 14.5%

C

Tetrapotassium ubiquinol-1,4-diphosphate: 0.5%
Sodium N-lauroylsarcosinate: 10.0%
Purified water: balance The components of A were mixed with each other, the components of B were mixed with each other, and the components of C were mixed with each other. The mixtures A and B were heated at 80° C. to dissolution. The mixture C formed a solution at normal temperature. The mixture B was added to the mixture A little by little while the mixture A was stirred, and the mixture C was admixed to the resultant mixture. Subsequently, the mixture was cooled with stirring. The stirring was stopped when the temperature was about 30° C. The mixture was allowed to stand to give a facial cleanser.

Prescription Example 24

A

Lauric acid: 2.0%
Myristic acid: 17.0%
Palmitic acid: 4.0%
Stearic acid: 4.0%
Coconut oil fatty acid potassium salt: 8.0%
Coconut oil fatty acid diethanolamide: 3.0%
Sodium N-methyl cocoyl taurate: 10.0%
Concentrated glycerin: 10.0%
1,3-butylene glycol: 10.0%
Tetrapotassium ubiquinol-1,4-diphosphate: 0.2%

B

Potassium hydroxide: 5.5%
Tetrasodium edentate: 0.2%
Purified water: balance

The components of A were mixed with each other, and the components of B were mixed with each other. The mixture A was heated at 80° C. to dissolution. The mixture B formed a solution at normal temperature. The mixture B was added to the mixture A little by little while the mixture A was stirred. Subsequently, the mixture was cooled with stirring. The stirring was stopped when the temperature was about 30° C. The mixture was allowed to stand to give a facial cleanser.

Example 16

Preparation of Shampoo

A shampoo was prepared based on the following prescription example 25. In the prescription example 25, the total of the components was 100%.

Prescription Example 25

Sodium POE(2) lauryl ether sulfate: 30.0%
Ammonium POE(2) lauryl ether sulfate: 20.0%
Betaine lauryldimethylaminoacetate: 6.0%
Chloro 0-[2-hydroxy-3-(trimethylammonio)propyl]hydroxyethyl cellulose: 0.25%
Coconut oil fatty acid diethanolamide: 4.0%
Ethylene glycol distearate: 2.0%
1,3-butylene glycol: 3.0%
Disodium edentate: 0.2%
Tetrapotassium ubiquinol-1,4-diphosphate: 0.5%
Purified water: balance

Example 17

Preparation of Hair Tonic

A hair tonic was prepared based on the following prescription example 26. In the prescription example 26, the total of the components was 100%.

Prescription Example 26

Salicylic acid: 0.3%
Menthol: 0.2%
Ethanol: 60.0%
Glycerin: 5.0%
Tetrapotassium ubiquinol-1,4-diphosphate: 1.0%
Purified water: balance The above components were mixed and dissolved at normal temperature to produce a hair tonic.

The invention claimed is:

1. A skin agent for external use comprising at least one component selected from the group consisting of potassium salts of ubiquinone derivatives,
   wherein the at least one component is present at a concentration in the range of 0.001 to 10% by mass of the skin agent, and
   wherein the potassium salts of ubiquinone derivatives are represented by the formula (1):

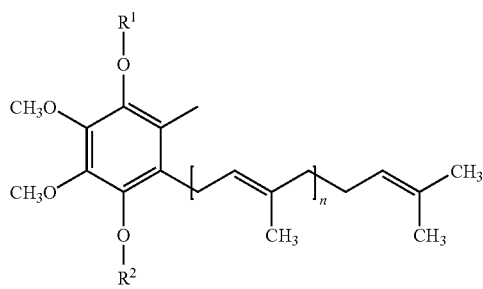

(1)

wherein $R^1$ and $R^2$ both phosphoric acid groups, and n is 9.

2. The skin agent for external use according to claim 1, wherein the skin agent for external use is an antioxidant skin agent for external use.

3. The skin agent for external use according to claim 1, wherein the skin agent for external use is an anti aging skin agent for external use.

4. The skin agent for external use according to claim 1, wherein the skin agent for external use is a skin roughness preventing skin agent for external use.

5. The skin agent for external use according to claim 1, wherein the skin agent for external use is a radical scavenger.

6. A cosmetic agent comprising at least one component selected from the group consisting of potassium salts of ubiquinone derivatives,
   wherein the at least one component is present at a concentration in the range of 0.001 to 10% by mass of the skin agent, and
   wherein the potassium salts of ubiquinone derivatives are represented by the formula (1):

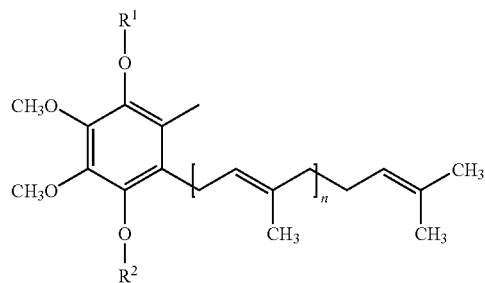

(1)

wherein $R^1$ and $R^2$ both phosphoric acid groups, and n is 9.

7. The cosmetic agent according to claim 6, wherein the cosmetic agent is an antioxidant cosmetic agent.

8. The cosmetic agent according to claim 6, wherein the cosmetic agent is an anti aging cosmetic agent.

9. The cosmetic agent according to claim 6, wherein the cosmetic agent is a skin roughness preventing cosmetic agent.

10. The cosmetic agent according to claim 6 wherein the cosmetic agent is a radical scavenger.

11. A method for supplying skin cells with at least one selected from the group consisting of ubiquinone derivatives, salts of the ubiquinone derivatives, ubiquinone and ubiquinol, the method comprised of topically applying to a subject in need thereof an effective amount of the skin agent of claim 1.

12. The method according to claim 11, wherein at least one of ubiquinone and ubiquinol is formed by dephosphorylation of the ubiquinone derivative or the salt thereof applied to the skin.

13. The method according to claim 11, wherein ubiquinone is formed by oxidation of ubiquinol.

14. A method for accelerating the regeneration of stratum corneum in the skin of a subject, the method comprised of topically applying to the subject in need thereof an effective amount of the skin agent of claim 1.

15. A method for improving skin roughness in the skin of a subject, the method comprised of topically applying to the subject in need thereof an effective amount of the skin agent of claim 1.

16. A method for slowing skin aging of a subject, the method comprised of topically applying to the subject in need thereof an effective amount of the skin agent of claim 1.

17. A method for scavenging radicals in the skin of a subject, the method comprised of topically applying to the subject in need thereof an effective amount of the skin agent of claim 1.

* * * * *